United States Patent
Jackson et al.

(10) Patent No.: US 9,278,154 B2
(45) Date of Patent: Mar. 8, 2016

(54) RESILIENT TAMPON AND METHOD FOR MAKING

(71) Applicant: Kimberly-Clark Worldwide, Inc., Neenah, WI (US)

(72) Inventors: David Martin Jackson, Alpharetta, GA (US); Clifford Jackson Ellis, Woodstock, GA (US); Candace Dyan Krautkramer, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 224 days.

(21) Appl. No.: 13/962,382

(22) Filed: Aug. 8, 2013

(65) Prior Publication Data

US 2013/0324960 A1 Dec. 5, 2013

Related U.S. Application Data

(62) Division of application No. 13/051,447, filed on Mar. 18, 2011, now Pat. No. 8,530,721.

(51) Int. Cl.
- *A61F 13/20* (2006.01)
- *A61L 15/28* (2006.01)
- *A61L 15/22* (2006.01)

(52) U.S. Cl.
CPC ............... *A61L 15/28* (2013.01); *A61F 13/206* (2013.01); *A61F 13/2051* (2013.01); *A61F 13/2088* (2013.01); *A61F 13/2094* (2013.01); *A61L 15/225* (2013.01)

(58) Field of Classification Search
CPC  A61F 13/2051; A61F 13/206; A61F 13/2094
See application file for complete search history.

(56) References Cited

U.S. PATENT DOCUMENTS

| | | | |
|---|---|---|---|
| 2,391,343 A | 12/1945 | Popper | |
| 3,914,822 A | 10/1975 | Wood | |
| 5,084,038 A | 1/1992 | Sheldon et al. | |
| 5,486,167 A * | 1/1996 | Dragoo | A61F 13/15203 604/358 |
| 5,755,906 A | 5/1998 | Achter et al. | |
| 5,836,930 A * | 11/1998 | Lantz | A61F 13/49012 604/378 |
| 5,891,123 A | 4/1999 | Balzar | |
| 6,595,974 B1 | 7/2003 | Pauley et al. | |
| 6,846,448 B2 | 1/2005 | Rymer et al. | |
| 6,939,340 B1 | 9/2005 | Berges | |
| 7,387,622 B1 | 6/2008 | Pauley et al. | |
| 7,678,095 B2 | 3/2010 | Jackson et al. | |
| 7,732,039 B2 | 6/2010 | Chakravarty et al. | |
| 7,790,640 B2 | 9/2010 | Chakravarty et al. | |
| 8,293,968 B2 | 10/2012 | Schmidt-Forst et al. | |
| 2001/0018391 A1 | 8/2001 | Hull et al. | |
| 2002/0169428 A1 * | 11/2002 | Fell et al. | 604/367 |
| 2003/0116888 A1 | 6/2003 | Rymer et al. | |

(Continued)

FOREIGN PATENT DOCUMENTS

WO    WO 2002/092898 A1    11/2002

*Primary Examiner* — Susan Su
(74) *Attorney, Agent, or Firm* — Kimberly-Clark Worldwide, Inc.

(57) ABSTRACT

A method of making a resilient tampon includes the steps of providing binder fibers having an average fiber length of at least 35 mm; combining the binder fibers to form a loose fleece; activating the binder fibers; and compressing a portion of the loose fleece into a pledget after activating the binder fibers.

A resilient tampon includes 70 wt % to 95 wt % absorbent fibers and 5 wt % to 30 wt % bicomponent binder fibers. The binder fibers have an average fiber length greater than 35 mm.

12 Claims, 3 Drawing Sheets

(56) References Cited

U.S. PATENT DOCUMENTS

| | | |
|---|---|---|
| 2003/0118814 A1 | 6/2003 | Workman et al. |
| 2003/0119400 A1 | 6/2003 | Beitz et al. |
| 2003/0119401 A1 | 6/2003 | Chakravarty et al. |
| 2003/0119402 A1 | 6/2003 | Melius et al. |
| 2003/0119405 A1 | 6/2003 | Abuto et al. |
| 2003/0119406 A1 | 6/2003 | Abuto et al. |
| 2003/0119413 A1 | 6/2003 | Chakravarty et al. |
| 2003/0129392 A1 | 7/2003 | Abuto et al. |
| 2004/0204698 A1 | 10/2004 | Zenker et al. |
| 2005/0256482 A1 | 11/2005 | Minoguchi et al. |
| 2006/0141891 A1 | 6/2006 | Melius et al. |
| 2006/0247592 A1 | 11/2006 | Schmidt-Forst et al. |
| 2007/0260211 A1 | 11/2007 | Schmidt-Forst |
| 2007/0266503 A1 | 11/2007 | Schmidt-Forst et al. |
| 2009/0177175 A1 | 7/2009 | Wang et al. |
| 2012/0283684 A1 * | 11/2012 | Schmidt-Foerst .... A61F 13/208 604/385.17 |

* cited by examiner

RESILIENT TAMPON AND METHOD FOR MAKING

BACKGROUND OF THE INVENTION

Currently, there are two basic types of tampons used for feminine hygiene. The first type is a digitally insertable tampon which is designed to be inserted directly by the user's fingers. The second type is an applicator style tampon which is designed to be inserted with the aid of an applicator. Both types are usually made by folding or rolling a loosely associated rectangular strip of absorbent material into a blank and then compressing the blank into a cylindrically-shaped product known as a pledget. The pledget may or may not have a cover. In both types, a withdrawal string is attached to the pledget before the tampon is wrapped and packaged for sale. In the applicator style tampon, the tampons are assembled into an applicator prior to being wrapped and packaged.

During packaging, storage, and insertion, there is a general desire for tampon pledgets to be relatively compact and compressed. However, in use there is a desire for the tampon pledgets to expand to more completely occupy the vaginal canal and prevent fluid leakage. The formation of typical pledgets can limit the subsequent expansion from the compressed state. To overcome this limitation, various efforts have been undertaken to incorporate a resilient material or resilient layer during formation of the pledget. While these materials and layers provide some resiliency, it tends to be lost over time. Thus, there is a need for a tampon that maintains its resiliency throughout the product life cycle from manufacture to disposal and a method for making.

SUMMARY OF THE INVENTION

In one aspect, the present invention provides a method of making a resilient tampon. The method includes the steps of providing binder fibers having an average fiber length of at least 35 mm, combining the binder fibers to form a loose fleece, activating the binder fibers, and compressing a portion of the loose fleece into a pledget after activating the binder fibers.

In some embodiments, the method may further include the steps of providing absorbent fibers and combining the absorbent fibers together with the binder fibers to form the loose fleece.

In various embodiments, the method may further include the steps of cutting the loose fleece into individual units and rolling, stacking, or folding the units into blanks before compressing the blanks into pledgets.

In some embodiments, the activating step may include heating the loose fleece at a temperature of 240 degrees F. to 330 degrees F. and the method may include the step of actively cooling the loose fleece after heating and before compressing.

In various embodiments, the absorbent fibers are viscose rayon. Likewise, in various embodiments, the binder fibers are bicomponent fibers.

In some embodiments, the loose fleece includes 80 wt % to 95 wt % absorbent fibers and 5 wt % to 20 wt % binder fibers. In some embodiments, the combining step includes carding the absorbent fibers and the binder fibers to form the loose fleece. In some embodiments, the combining step includes dry laying the absorbent fibers and the binder fibers to form the loose fleece.

In another aspect, the present invention provides a method of making a resilient tampon. The method includes the steps of providing viscose rayon fibers and providing bicomponent binder fibers having an average fiber length of at least 35 mm. The method further includes the step of combining the viscose rayon fibers together with the bicomponent binder fibers to form a loose fleece having 5 wt % to 30 wt % bicomponent binder fibers and 70 wt % to 95 wt % viscose rayon fibers. The method further includes the steps of activating the bicomponent binder fibers by heating the loose fleece at a temperature of 240 degrees F. to 330 degrees F. and then actively cooling the loose fleece after activating. The method further includes the steps of cutting the loose fleece into individual units after cooling; rolling, stacking, or folding the individual units into blanks after cutting; and compressing the individual blanks into pledgets after rolling, stacking, or folding.

In various embodiments, the activating step includes heating via convection. In some embodiments, the combining step includes carding the viscose rayon fibers and the bicomponent binder fibers together to form the loose fleece. In some embodiments, the combining step includes dry laying the viscose rayon fibers and the bicomponent binder fibers together to form the loose fleece.

In some embodiments, no additional external heat is applied to the pledget during the compressing step.

In another aspect, the present invention provides a resilient tampon. The resilient tampon includes 70 wt % to 95 wt % absorbent fibers and 5 wt % to 30 wt % bicomponent binder fibers, wherein the binder fibers have an average fiber length greater than 35 mm.

In some embodiments, the absorbent fibers are viscose rayon and comprise 85 wt % to 90 wt %. In some embodiments, the bicomponent binder fibers comprise 10 wt % to 15 wt % and have a core made of polypropylene and a sheath made of modified polyethylene, wherein the sheath surrounds the core.

In some embodiments, the absorbent fibers are trilobal viscose rayon and comprise 85 wt % to 90 wt %, the bicomponent binder fibers comprise 10 wt % to 15 wt % and have a core made of polypropylene and a sheath made of modified polyethylene, wherein the sheath surrounds the core, and the absorbent fibers and the bicomponent fibers are substantially aligned.

DETAILED DESCRIPTION OF THE DRAWINGS

The tampon of the present invention is designed to be inserted above the introital region of a woman's vagina and is designed to function so as to intercept the fluid flow of menses, blood, and other body fluids and prevent the fluid from exiting the vagina. As compared to traditional compressed tampons, the tampon of the present invention is manufactured to be more resilient to compression and thus more expandable when inserted. Dry expansion of the tampon is beneficial in that the tampon does not have to be wetted by body fluid before the tampon is capable of expanding.

While the pledgets of the present invention are described for use as a menstrual device, it will be readily apparent that the pledgets may also be used as any other suitable vaginal insert, such as a pessary. Likewise, while the pledgets of the present invention are generally described as being "absorbent", it will be readily apparent that the pledgets may be coated or otherwise treated to be partially or completely non-absorbent.

Figure 1:
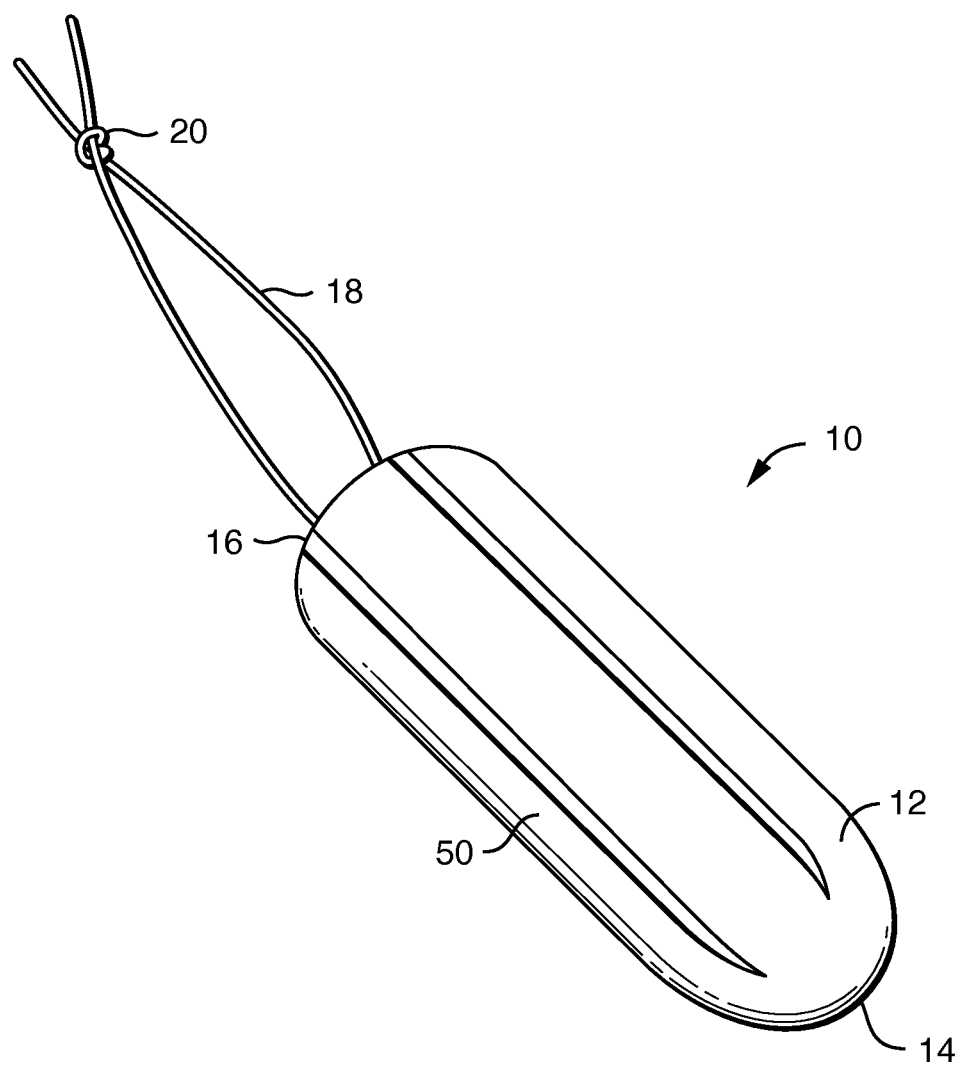
FIG. 1 representatively illustrates an exemplary tampon of the present invention.

As is shown in FIG. 1, an exemplary tampon 10 includes a mass of fibrous material 12 compressed into a generally cylindrically-shaped pledget 50. The tampon 10 generally has an insertion end 14 and a trailing end 16, wherein the insertion end 14 is designed to be the first part of the tampon which enters the woman's vaginal cavity. While in use, the pledget 50 of the present invention is designed to be entirely positioned within the woman's vagina.

The tampon 10 further includes a withdrawal string 18 for assisting in removing the tampon 10 from the woman's vagina. The withdrawal string 18 may be attached to the pledget 50 in any suitable manner. The withdrawal string 18 may further include one or more knots 20 to prevent fraying of the withdrawal string 18 and to provide a point where a woman can grasp the withdrawal string 18 when she is ready to remove the tampon 10 from her vagina.

Figure 2:
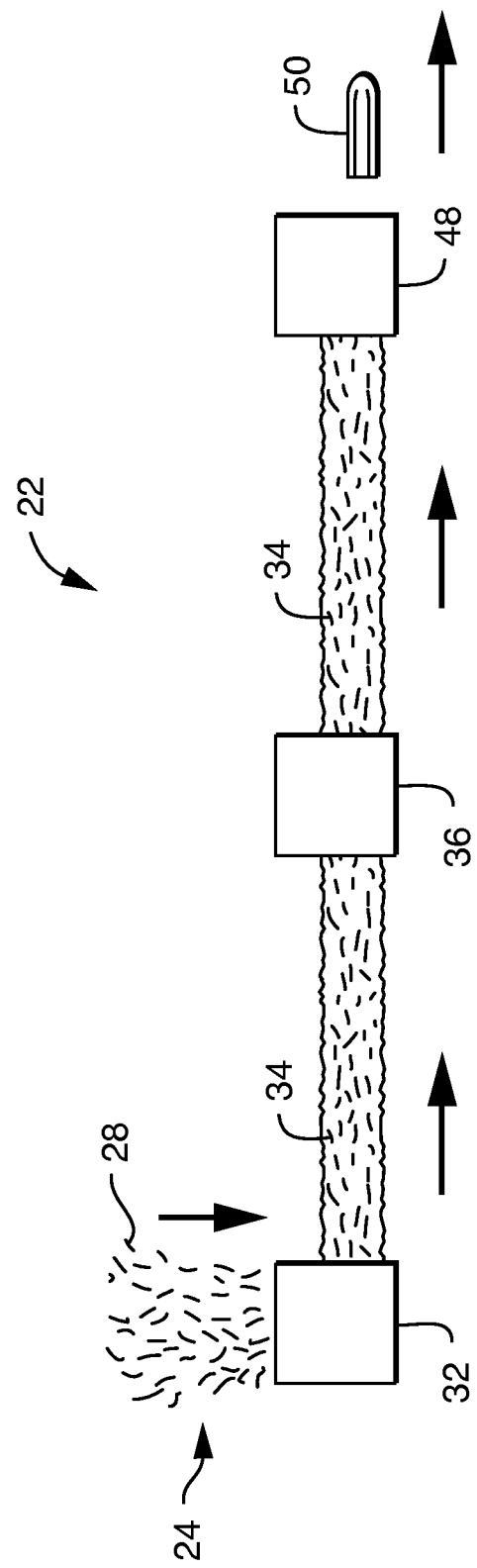
FIG. 2 schematically illustrates a first exemplary method of the present invention.

The tampon 10 of the present invention may be manufactured by providing binder fibers having an average fiber length of at least 35 mm, combining the binder fibers to form a loose fleece, activating the binder fibers, and compressing a portion of the loose fleece into a pledget after activating the binder fibers. Referring now to FIG. 2, a method 22 for making a resilient tampon 10 is representatively illustrated. The method 22 includes the step 24 of providing binder fibers 28 having an average fiber length of at least 35 mm. The binder fibers 28 are combined in the step 32 to form a loose fleece 34. After the loose fleece 34 is formed, the method 22 further includes the step 36 of activating the binder fibers 28. Finally, the method 22 includes the step 48 of compressing a portion of the loose fleece 34 into a pledget 50.

The binder fibers 28 may be any suitable fibers, such as bicomponent fibers. As used herein, the term "bicomponent fibers" refers to fibers which have been formed from at least two different polymers extruded from separate extruders but spun together to form one fiber. Bicomponent fibers are also sometimes referred to as conjugate fibers or multicomponent fibers. The polymers of the bicomponent fibers are arranged in substantially consistent and distinct zones across the cross-section of the bicomponent fibers and extend continuously along the length of the bicomponent fibers. The bicomponent fibers may be configured in any suitable manner. For example, the bicomponent fibers may have a sheath/core arrangement wherein one polymer is surrounded by another, or may be a side-by-side arrangement, a pie arrangement, or an "islands-in-the-sea" arrangement. Exemplary bicomponent fibers are disclosed in U.S. Pat. No. 5,108,820 to Kaneko et al., U.S. Pat. No. 4,795,668 to Krueger, et al., U.S. Pat. No. 5,540,992 to Marcher et al., and U.S. Pat. No. 5,336,552 to Strack et al. Bicomponent fibers are also taught by U.S. Pat. No. 5,382,400 to Pike et al., and may be used to produce crimp in the fibers by using the differential rates of expansion and contraction of the two (or more) polymers.

For two component bicomponent fibers, the polymers are desirably present in any suitable weight ratio, such as 75/25 to 25/75. In some embodiments, the weight ratio of the polymers may be 60/40 or 50/50. Suitable bicomponent fibers may have a sheath/core configuration wherein the sheath is generally softer and has a lower bonding temperature making it suitable for thermoplastic or physical bonding to other fibers. In comparison, the core generally has a higher melting temperature, does not melt during bonding, and provides a structural fiber network that provides strength and resiliency to the fleece and ultimately the pledget. In various embodiments, the sheath may be made of any suitable polymer, such as polyethylene. Likewise, the core may be made of any suitable polymer, such as polypropylene or polyester. In some embodiments, the sheath/core bicomponent fibers may have a weight ratio of 60/40 or 50/50 polyethylene to polypropylene.

The binder fibers 28 have an average fiber length of at least 35 mm. While not wishing to be bound by theory, it is believed that providing binder fibers of this length provides for a resilient, liquid stable and three-dimensional network of physically bonded fibers having fibers with multiple bond points. This network of binder fibers is believed to provide stored energy to drive expansion after compression into pledgets. The use of longer binder fibers results in an effective compressed network with a lower binder fiber percentage. This lower binder fiber percentage helps reduce cost and enables smaller tampons (i.e., more fibers used for absorbency and less for resiliency). The longer binder fibers are also believed to create a binder fiber network that is interpenetrated with an absorbent fiber network. The absorbent fiber network is stabilized by both the binder fiber network and the hydrogen bonding that occurs during compression. This interpenetration of fiber networks is believed to reduce the aging effect on the resilient character of the liquid stable network (i.e., binder fiber network). In contrast, separate resilient materials and layers do not have these two interpenetrated fiber networks. Thus, the resilient materials and layers are believed to lose much of their resiliency over time.

In some embodiments, the present invention may further include the step of providing other fibers in addition to the binder fibers 28. For example, to create an absorbent fiber network, some embodiments may further include the step of providing absorbent fibers and combining the absorbent fibers together with the binder fibers to form the loose fleece 34. Thus, the fleece 34, and ultimately the pledget 50, may include a combination of absorbent fibers and binder fibers 28. The absorbent fibers may include any suitable absorbent material made from artificial or natural fibers, such as polyester, cellulose, acetate, nylon, polypropylene, rayon, cotton or blends thereof. The absorbent fibers may also include any suitable blend of fibers. For example, the absorbent fibers can be formed from cellulosic fibers, such as cotton and rayon. The absorbent fibers can be 100 wt % cotton, 100 wt % rayon, or a blend of cotton and rayon fibers. In some embodiments, the cellulose fibers may be modified for super-absorbency.

When cotton fibers are used, the cotton fibers should have a staple length of between about 20 millimeters (mm) to about 40 mm. The cotton fibers should generally have a fiber size of between about 15 microns to about 28 microns. The cotton fibers can also be bleached if desired. Bleaching will make the cotton fibers whiter in appearance.

When rayon fibers are present, the rayon fibers should have a staple length of between about 20 mm to about 45 mm. In some embodiments, rayon fibers may have a staple length of 38-42 mm. Suitable rayon fibers may have a denier of between about 1 to about 6. In specific embodiments, the rayon fibers may be viscose rayon, lyocell rayon, or any other suitable rayon or regenerated cellulose.

The rayon fibers may have a circular, bi-lobal, or tri-lobal cross-sectional configuration, or some other cross-sectional configuration known to those skilled in the art. The bi-lobal configuration has a cross-sectional profile which looks like a dogbone while the tri-lobal configuration has a cross-sectional profile which looks like a "Y". The rayon fibers can also be bleached if desired.

The various fibers of the present invention may be combined in any suitable manner. Specifically, the combination step 32 may include any suitable web forming process and apparatus to produce the loose fleece 34. For example, the combination step 32 may include forming a bonded carded web, a dry laid web, or the like.

Bonded carded webs are made from staple fibers. Typically the fibers are longer than 20, 30, or 35 mm. The fibers are usually purchased in bales. The bales are placed in a picker, which separates the fibers. Then, the fibers are sent through a combing or carding unit, which further breaks apart and aligns the staple fibers in the machine direction to form a generally machine direction-oriented fibrous nonwoven web. Once the web is formed, it is then bonded by one or more of several known bonding methods, such as through air bonding or pattern bonding.

Dry laid webs are also made from staple fibers. Typically the fibers are 20 mm or longer. In dry laying, fibers or tufts of fibers of a first type (e.g., absorbent fibers) are fed to a first rotating vacuum drum and fibers or tufts of fibers of a second type (e.g., binder fibers) are fed to a second rotating vacuum drum. The different fibers are laid down by suction to form mats of fibers. The mats of fibers are doffed from the vacuum drums and are then combed via rotating lickerins. The lickerins have peripheral teeth which comb the different fibers from the mat. The combed fibers are doffed from the lickerins via centrifugal force and into a fiber mixing and expansion chamber. The mixed fibers are deposited on an endless vacuum screen to form a random fiber web comprised of first and second fiber types. The flow and velocity of each independent fiber stream can be controlled to provide the desired quantity of each fiber type.

In various embodiments, the fleece 34 and the resultant pledgets 50 may have any suitable combination and ratio of fibers. For example, in some embodiments, the fleece 34 and the resultant pledgets 50 may include 70 wt % to 95 wt % absorbent fibers and 5 wt % to 30 wt % binder fibers. In some embodiments, the fleece 34 and the resultant pledgets 50 may include 80 wt % to 90 wt % absorbent fibers and 10 wt % to 20 wt % binder fibers. In other embodiments, the fleece 34 and the resultant pledgets 50 may include 85 wt % absorbent fibers and 15 wt % binder fibers. In some embodiments, the fleece 34 and the resultant pledgets 50 may include 80 wt % to 90 wt % trilobal viscose rayon and 10 wt % to 20 wt % bicomponent binder fibers. In other embodiments, the fleece 34 and the resultant pledgets 50 may include 85 wt % trilobal viscose rayon fibers and 15 wt % bicomponent binder fibers.

In some embodiments, the fleece 34 may optionally be further manipulated before the activating step 36. For example, the fleece 34 may be folded, corrugated, or otherwise processed before the activating step 36.

The activating step 36 may include any suitable means of heating the binder fibers 28. For example, the activating step 36 may include convection heating, through air heating, superheated steam, microwave heating, radiant heating, radio frequency heating, and the like, and combinations thereof. In some embodiments, the activating step 36 may include heating the fleece 34 at a temperature of 240 degrees F. to 330 degrees F. (115-165 C.) to activate the binder fibers 28. During activation, the binder fibers 28 soften and become tacky and thus bind to adjacent fibers creating a three-dimensional fiber matrix. The three-dimensional fiber matrix acts to stabilize the fleece 34. This three-dimensional fiber matrix creates a liquid stable network.

In some embodiments, the activating step 36 may be followed by a cooling step. The cooling step may utilize any suitable means for reducing the temperature of the fleece 34. For example, the fleece 34 may be cooled by simply allowing the fleece 34 to return to ambient temperature over a period of time. Likewise, the fleece 34 may be actively cooled with chill rolls, cooling chambers, blowing conditioned air, or the like, or combinations thereof. The cooling step is undertaken before the compressing step to set the binder fibers 28 and ensure the binder fibers 28 and the absorbent fibers 30 have established a wet-stable three-dimensional structure before compression.

In various embodiments, the present invention may include the step of cutting the stabilized fleece 34 into individual units and rolling, stacking, folding, or otherwise manipulating one or more of the individual units into blanks before compressing the blanks into pledgets. For example, suitable menstrual tampons may include "cup" shaped pledgets like those disclosed in U.S. publication 2008/0287902 to Edgett and U.S. Pat. No. 2,330,257 to Bailey; "accordion" or "W-folded" pledgets like those disclosed in U.S. Pat. No. 6,837,882 to Agyapong; "radially wound" pledgets like those disclosed in U.S. Pat. No. 6,310,269 to Friese; "sausage" type or "wad" type pledgets like those disclosed in U.S. Pat. No. 2,464,310 to Harwood; "M-folded" tampon pledgets like those disclosed in U.S. Pat. No. 6,039,716 to Jessup; "stacked" tampon pledgets like those disclosed in U.S. 2008/0132868 to Jorgensen; or "bag" type tampon pledgets like those disclosed in U.S. Pat. No. 3,815,601 to Schaefer.

A suitable method for making "radial wound" pledgets is disclosed in U.S. Pat. No. 4,816,100 to Friese. The radial winding method may also include a method for compressing the blank into a pledget like that disclosed in U.S. Pat. No. 6,310,269 to Friese. Suitable methods for making "W-folded" pledgets are disclosed in U.S. Pat. No. 6,740,070 to Agyapong; U.S. Pat. No. 7,677,189 to Kondo; and U.S. 2010/0114054 to Mueller. A suitable method for making "cup" pledgets and "stacked" pledgets is disclosed in U.S. application 2008/0132868 to Jorgensen.

In various embodiments, the present invention includes the step 48 of compressing a portion of the fleece 34 (i.e., a blank) into a pledget 50. The compressing step 48 may utilize any suitable means and apparatus. For example, the compressing step 48 may utilize a plurality of dies which reciprocate relative to one another so as to form a mold cavity there between. When the blank (e.g., a softwind) is positioned within the mold cavity, the dies may be actuated so as to move towards one another and compress the blank. The blank may be compressed any suitable amount. For example, the blank may be compressed at least 25%, at least 50%, at least 100%, or at least 150% of the initial dimensions. For example, softwind blanks may be reduced in diameter to approximately ¼ of the original diameter. The cross-sectional configuration of the resultant pledgets 50 may be circular, ovular, rectangular, hexagonal, or any other suitable shape.

In various embodiments, the compressing step 48 does not include any additional heat applied to the pledget 50. In other words, the blank is compressed into a pledget 50 without external heat being applied to the compression equipment or the blank. In various embodiments, the compressing step 48 may incorporate or may be followed by one or more additional stabilization steps. This secondary stabilization serves to maintain the compressed shape of the pledget. In general, the secondary stabilization step may create hydrogen bonds between the absorbent fibers and/or may further strengthen the entanglement of the absorbent fibers to maintain the shape of the compressed pledget 50.

Figure 3:
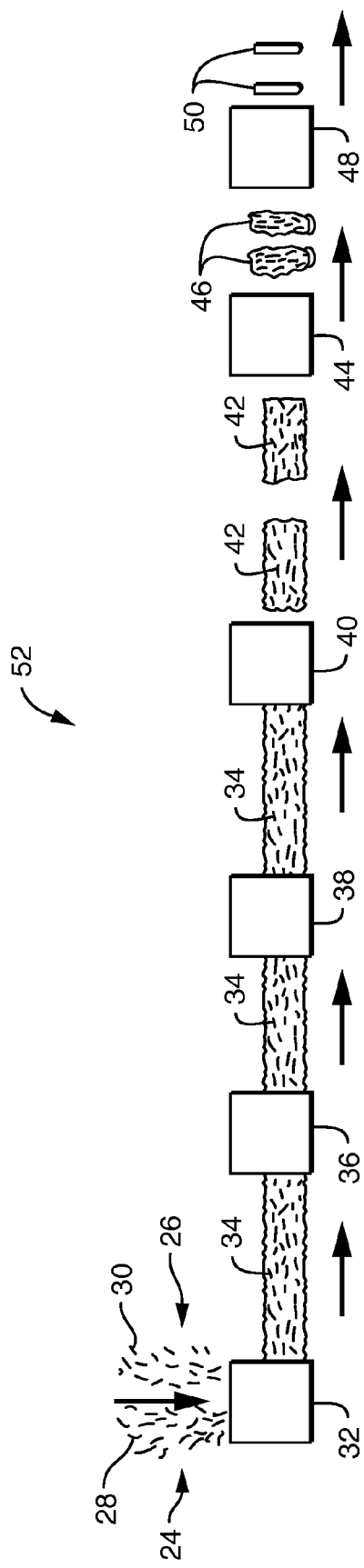
FIG. 3 schematically illustrates a second exemplary method of the present invention.

Referring now to FIG. 3, another exemplary method 52 for making a resilient tampon 10 is representatively illustrated. The method 52 includes the step 24 of providing binder fibers 28 and the step 26 of providing absorbent fibers 30. The absorbent fibers 30 may be viscose rayon fibers or any other suitable absorbent fibers or fiber combinations. Likewise, the binder fibers 28 may be bicomponent binder fibers having an average fiber length of at least 35 mm or any other suitable binder fibers or fiber combinations.

The method 52 further includes the step 32 of combining the binder fibers 28 and the absorbent fibers 30 together to form a loose fleece 34. The combining step 32 may include any suitable means for forming fibers into fibrous webs. The binder fibers 28 and the absorbent fibers 30 may be added in any suitable ratio to provide the desired ratio in the fleece 34 and the resultant pledgets 50.

The method 52 further includes the step 36 of activating the binder fibers 28 by heating the loose fleece 34 at a temperature of 240 degrees F. to 330 degrees F. The activating step 36 may utilize any suitable heating mechanism to effect physical bonding of the binder fibers 28 with the surrounding fibers. After heating the fleece 34, the method 52 further includes the step 38 of cooling the fleece 34. As discussed herein, the cooling step 38 may include active cooling, passive cooling, or combinations thereof. The activating step 36 and the cooling step 38 serve to stabilize the fleece 34 and create an interpenetrated binder fiber network and absorbent fiber network.

The method 52 further includes the step 40 of cutting the fleece 34 into individual units 42. The cutting step 40 may utilize any suitable method of separating the fleece 34 into individual units 42. For example, the cutting step 40 may include a die cutter, knife and anvil rolls, and the like.

After the individual units 42 are separated, the method 52 further includes the step 44 of rolling, stacking, folding, or otherwise manipulating one or more individual units 42 into blanks 46. For example, one or more individual units 42 may be rolled into a blank using traditional radial winding techniques and apparatus. Likewise, multiple individual units 42 may be stacked to form a blank 46.

Finally, the method 52 includes the step 48 of compressing the blanks 46 into pledgets 50. In various embodiments, the compressing step 48 is completed in the absence of any externally added heat. During or after the compression step 48, the insertion end 14 of the pledget 50 can be rounded to facilitate insertion into a woman's vagina, while the trailing end 16 may be relatively flat. The rounding of the insertion end 14 is normally done during compression and is optional but is generally preferred by the consumer.

In various embodiments, the pledgets 50 may be subject to further processing to result in a finished tampon 10. For example, the pledgets 50 may be joined with a withdrawal string 18 and/or cover and/or applicator.

The resilient tampon 10 of the present invention may include 70 wt % to 95 wt % absorbent fibers and 5 wt % to 30 wt % bicomponent binder fibers having an average fiber length greater than 35 mm. In some embodiments, the resilient tampon 10 may include 10 wt % to 15 wt % bicomponent fibers, wherein the core is made of polypropylene and the sheath is made of modified polyethylene. In some embodiments, the resilient tampon 10 may include 80 wt % to 90 wt % trilobal viscose rayon fiber and 10 wt % to 20 wt % bicomponent binder fiber. In some embodiments, the viscose rayon fibers and the bicomponent binder fibers may be substantially aligned.

In various embodiments, the tampons may also include one or more additional features. For example, the tampons may include a "protection" feature as exemplified by U.S. Pat. No. 6,840,927 to Hasse, U.S. 2004/0019317 to Takagi, U.S. Pat. No. 2,123,750 to Schulz, and the like. In some embodiments, the tampons may include an "anatomical" shape as exemplified by U.S. Pat. No. 5,370,633 to Villalta, an "expansion" feature as exemplified by U.S. Pat. No. 7,387,622 to Pauley, an "acquisition" feature as exemplified by U.S. 2005/0256484 to Chase, an "insertion" feature as exemplified by U.S. Pat. No. 2,112,021 to Harris, a "placement" feature as exemplified by U.S. Pat. No. 3,037,506 to Penksa, or a "removal" feature as exemplified by U.S. Pat. No. 6,142,984 to Brown.

In various embodiments, the pledget 50 may be further processed to include a withdrawal string 18 and/or cover and may further be inserted into an applicator prior to packaging. The optional cover can be formed from a nonwoven material such as a polyolefin, particularly polypropylene or polyethylene. The cover material may be spunbond. The cover may be beneficial in assuring that the fibers of the pledget 50 do not directly contact the inner walls of a woman's vagina. This minimizes the likelihood that fibers will be left behind in the vagina after the tampon 10 has been removed. The cover may be tucked into the insertion end 14 and/or the trailing end 16 so as to substantially or completely surround and enclose the absorbent fibers. The cover can also be constructed from a heat-sealable material to assist in bonding all or portions of it to the pledget, such as by heat and/or pressure.

The withdrawal string 18 may be attached to the pledget 50 in any suitable manner. For example, an opening can be formed through the pledget 50 (and cover if provided) so as to provide a means for attaching a withdrawal string 18. In various embodiments, the withdrawal string 18 may be attached to the fibrous material 12 before or after it is compressed into the pledget 50. The withdrawal string 18 may be attached to the fibrous material 12 and then looped upon itself. A knot 20 can then be formed near the free ends of the withdrawal string 18 to assure that the string 18 does not separate from the fibrous material 12. The knot 20 also serves to prevent fraying of the withdrawal string 18 and to provide a place or point where a woman can grasp the withdrawal string 18 when she is ready to remove the tampon 10 from her vagina.

The withdrawal string 18 can be constructed from various types of threads or ribbons. A thread or ribbon may be made from 100 percent cotton fibers and/or other materials in whole or part. The string may be bonded to the absorbent with or without tying. The withdrawal string 18 may have any suitable length and/or the withdrawal string 18 can be dyed and/or treated with an anti-wicking agent, such as wax, before being secured to the pledget 50.

While the invention has been described in detail with respect to specific embodiments thereof, it will be appreciated that those skilled in the art, upon attaining understanding of the foregoing will readily appreciate alterations to, variations of, and equivalents to these embodiments. Accordingly, the scope of the present invention should be assessed as that of the appended claims and any equivalents thereto. Additionally, all combinations and/or sub-combinations of the disclosed embodiments, ranges, examples, and alternatives are also contemplated.

The invention claimed is:

1. A resilient tampon comprising:
   a. 70 wt % to 95 wt % absorbent fibers; and
   b. 5 wt % to 30 wt % binder fibers, wherein the binder fibers have an average fiber length of greater than 35 mm;
      wherein the absorbent fibers and the binder fibers are substantially aligned.

2. The resilient tampon of claim 1 wherein the absorbent fibers are viscose rayon.

3. The resilient tampon of claim 2 wherein the absorbent fibers comprise 80 wt % to 90 wt %.

4. The resilient tampon of claim 1 wherein the absorbent fibers are trilobal viscose rayon.

5. The resilient tampon of claim 4 wherein the absorbent fibers comprise 80 wt % to 90 wt %.

6. The resilient tampon of claim 1 wherein the binder fibers are bicomponent fibers.

7. The resilient tampon of claim 6 wherein the bicomponent fibers comprise 10 wt % to 20 wt %.

8. The resilient tampon of claim 6 wherein the bicomponent fibers have a core made of polypropylene and a sheath made of modified polyethylene wherein the sheath surrounds the core.

9. A resilient tampon comprising,
   a. 70 wt % to 95 wt % absorbent fibers; and
   b. 5 wt % to 30 wt % bicomponent binder fibers, wherein the binder fibers have an average fiber length greater than 35 mm;
      wherein the absorbent fibers and the bicomponent binder fibers are substantially aligned.

10. The resilient tampon of claim 9 wherein the absorbent fibers are viscose rayon and comprise 85 wt % to 90 wt %.

11. The resilient tampon of claim 9 wherein the bicomponent binder fibers comprise 10 wt % to 15 wt % and have a core made of polypropylene and a sheath made of modified polyethylene wherein the sheath surrounds the core.

12. The resilient tampon of claim 9 wherein
   a. the absorbent fibers are trilobal viscose rayon and comprise 80 wt % to 90 wt %; and
   the bicomponent fibers comprise 10 wt % to 20 wt % and have a core made of polypropylene and a sheath made of modified polyethylene wherein the sheath surrounds the core.

* * * * *